US012758403B2

(12) United States Patent
Horstmann et al.

(10) Patent No.: US 12,758,403 B2
(45) Date of Patent: Oct. 13, 2026

(54) BIONIC JOINT AND A PROSTHESIS FOR REPLACING AN ELBOW JOINT

(71) Applicant: TECHNISCHE UNIVERSITÄT MÜNCHEN, Munich (DE)

(72) Inventors: Bart Horstmann, Delft (NL); Theophil Spiegeler Castaneda, Munich (DE); Cristina Piazza, Munich (DE)

(73) Assignee: Technische Universität München, Munich (DE)

( * ) Notice: Subject to any disclaimer, the term of this patent is extended or adjusted under 35 U.S.C. 154(b) by 465 days.

(21) Appl. No.: 18/377,617

(22) Filed: Oct. 6, 2023

(65) Prior Publication Data

US 2024/0122728 A1 Apr. 18, 2024

(30) Foreign Application Priority Data

Oct. 14, 2022 (EP) .................................... 22201644

(51) Int. Cl.
*A61F 2/58* (2006.01)
*A61F 2/70* (2006.01)

(52) U.S. Cl.
CPC ................ *A61F 2/582* (2013.01); *A61F 2/70* (2013.01); *A61F 2220/0025* (2013.01)

(58) Field of Classification Search
CPC .......... A61F 2/582; A61F 2/64; A61F 2/6607; A61F 2/54; A61F 2/60; A61F 2/604; A61F 2002/5093; B25J 9/0078; B25J 9/104
See application file for complete search history.

(56) References Cited

U.S. PATENT DOCUMENTS 6,699,290 B1 3/2004 Wack et al.
9,849,003 B2 * 12/2017 Rastgaar .................. A61F 2/70
(Continued)

FOREIGN PATENT DOCUMENTS

CN 118789533 A * 10/2024 ............ B25J 9/1612
CN 119347740 A * 1/2025 .......... B25J 17/0283
(Continued)

OTHER PUBLICATIONS

"Steeper Group Espire Pro Elbow" Brochure [online] Retrieved from the internet [retrieved on May 9, 2024] <URL: https://www.steepergroup.com/prosthetics/upper-limb-prosthetics/espire%E2%84%A2-elbow/models/espire-pro/>, 12 pages.
(Continued)

*Primary Examiner* — Alvin J Stewart
(74) *Attorney, Agent, or Firm* — Barclay Damon LLP

(57) ABSTRACT

An artificial joint for a prosthesis or robot arm, the artificial joint comprising a first rigid link, a second rigid link, a compliant joint rotatably connecting the first rigid link and the second rigid link with respect to a principal plane of rotation, and comprising an elastic link extending between the first rigid link and the second rigid link, and a first string section and a second string section both extending between the first rigid link and the second rigid link, being arranged on opposite sides with respect to the compliant joint, such that shortening one of the first string section and of the second string section and lengthening the other one of the first string section and of the second string section drives a rotation of the first rigid link and the second rigid link with respect to each other in the principal plane of rotation.

19 Claims, 5 Drawing Sheets

(56) References Cited

U.S. PATENT DOCUMENTS

| | | | | |
|---|---|---|---|---|
| 2012/0157100 | A1 | 6/2012 | Suzuki et al. | |
| 2015/0265425 | A1* | 9/2015 | Aagaah | A61F 2/80 623/47 |
| 2019/0328550 | A1 | 10/2019 | Akhtar et al. | |
| 2020/0121478 | A1 | 4/2020 | Woge et al. | |

FOREIGN PATENT DOCUMENTS

| | | | | | |
|---|---|---|---|---|---|
| CN | 119897899 | A | * | 4/2025 | B25J 9/104 |
| CN | 120816533 | A | * | 10/2025 | B25J 9/104 |
| EP | 4353199 | A1 | * | 4/2024 | A61F 2/58 |
| KR | 20210054844 | A | * | 5/2021 | A61F 2/64 |
| KR | 20240160330 | A | * | 11/2024 | F16D 69/02 |
| KR | 20260019704 | A | * | 2/2026 | B25J 9/104 |
| SU | 971312 | A1 | | 11/1982 | |
| WO | 2011028088 | A1 | | 3/2011 | |
| WO | 2022174087 | A1 | | 8/2022 | |

OTHER PUBLICATIONS

Bennett et al., "Design and Characterization of a Powered Elbow Prosthesis," 2015 37th Annual International Conference of the IEEE Engineering in Medicine and Biology Society (EMBC) pp. 2458-2461 (2015), 4 pages.
Bilancia et al., "Design of a bio-inspired contact-aided compliant wrist," Robotics and Computer Integrated Manufacturing 67:102028 (2021), 10 pages.
Binedell et al., "Design and development of a novel 3D-printed non-metallic self-locking prosthetic arm for a forequarter amputation," Prosthetics and Orthotics International 45(1):p. 94-99 (2021), 2 pages.
Capsi-Morales et al., "Comparison between rigid and soft poly-articulated prosthetic hands in non-expert myo-electric users shows advantages of soft robotics," Nature Scientific Reports 11:23952 (2021), 15 pages.
Capsi-Morales et al., "Exploring the Role of Palm Concavity and Adaptability in Soft Synergistic Robotic Hands," IEEE Robotics and Automation Letters, vol. 5, No. 3, pp. 4703-4710 (2020), 8 pages.
Casolo et al., "Functional Design of a Transmission for a Myoelectric Elbow Prosthesis," Proc. of the World Contress on Engineering 2008, vol. III, WCE 2008, Jul. 2-4, 2008, London, UK, 6 pages.
Catalano et al., "Adaptive Synergies for a Humanoid Robot Hand," 2012 12th IEEE-RAS Int'l Conf on Humanoid Robots, Nov. 29-Dec. 1, 2012, Business Innovation Center, Osaka, Japan (2012), 8 pages.
Catalano et al., "Adaptive synergies for the design and control of the Pisa/IIT SoftHand," Int'l Journal of Robotics Research 33(5):768-782 (2014), 15 pages.
Chatterjee et al., "Design of Above Elbow Prosthesis articulated with Electro-myogram signal and electrical switch," Journal of Scientific & Industrial Research, vol. 78, pp. 535-540 (2019), 6 pages.
Fillauer LLC "Motion E2 Elbow," [online] Retrieved from the Internet <URL: https://fillauer.com/products/motion-e2-elbow/> [retrieved on May 7, 2024], 3 pages.
Godfrey et al., "SoftHand at the CYBATHLON: A user's experience," Journal of NeuroEngineering and Rehabilitation 14:124 (2017), 12 pages.
Hernandez-Cerero et al., "Design and Analysis of 2 DOF Elbow Prosthesis," In: Zeghloul et al. (eds) Advances in Service and Industrial Robotics, RAAD 2021, Mechanisms and Machine Science, vol. 102, Springer, Cham. (2021), 10 pages.
Johannes et al., "An Overview of the Developmental Process for the Modular Prosthetic Limb," Johns Hopkins APL Technical Digest, vol. 30, No. 3, pp. 207-216 (2011), 10 pages.
Jonsson et al., "Osseointegration amputation prostheses on the upper limbs: methods, prosthetics and rehabilitation," Prosthetics and Orthotics International 35(2): 190-200 (2011), 11 pages.
Leal-Naranjo et al., "Mechanical Design and Assessment of a Low-Cost 7-DOF Prosthetic Arm for Shoulder Disarticulation," Hindawi, Applied Bionics and Biomechanics, vol. 2018, Article IDS 4357602 (2018), 13 pages.
Lemerle et al., "A Variable Stiffness Elbow Joint for Upper Limb Prosthesis," 2019 IEEE/RSJ Int'l Conf on Intelligent Robots and Systems (IROS), Macau, China, Nov. 4-8, 2019, 8 pages.
Lenzi et al., The RIC Arm—A Small Athropomorphic Transhumeral Prosthesis, IEEE/ASME Trans on Mechatronics, vol. 21, No. 6, pp. 2660-2671 (2016), 12 pages.
Li et al., "The Prosthetic Arm: A Dramatic Improvement for the Limb Amputation from the Humerus," 2019 IEEE 4th Conf on Advanced Robotics and Mechatronics (ICARM), Toyonaka, Japan, pp. 475-480 (2019), 6 pages.
Mobius Bionics, "LUKE Arm Detail Page," [online] Retrieved from the Internet <URL:https://mobiusbionics.com/luke-arm/#section-five>, [retrieved on May 7, 2024], 6 pages.
Montagnani et al., "A passive wrist with switchable stiffness for a body-powered hydraulically actuated hand prosthesis," 2017 Int'l Conf on Rehabilitation Robots (ICORR), QEII Centre, London, UK (2017), 6 pages.
Montagnani et al., "Preliminary Design and Development of a two Degrees of Freedom passive compliant prosthetic wrist with switchable stiffness," Proc. IEEE Int'l Conf on Robotics and Biomimetics (ROBIO), Shenzhen, China (2013), 6 pages.
Ottobock "DynamicArm Plus," Product Information [online] Retrieved from the Internet <URL: https://www.ottobock.com/en-us/product/12K110N> [retrieved on May 10, 2024], 9 pages.
Piazza et al., "A Century of Robotic Hands," Annual Review of Control, Robotics, and Autonomous Systems 2:1-32 (2019), 34 pages.
Piazza et al., "Exploring augmented grasping capabilities in a multi-synergistic soft bionic hand," Journal of NeuroEngineering and Rehabilitation 17:116 (2020), 16 pages.
Piazza et al., "SoftHand Pro-D: Matching Dynamic Content of Natural User Commands with Hand Embodiment for Enhanced Prosthesis Control," 2016 IEEE Int'l Conf on Robotics and Automation (ICRA), Stockholm, Sweden, May 16-21, 2016, pp. 3516-3523 (2016), 8 pages.
Piazza et al., "The SoftHand Pro-H: A Hybrid Body-Controlled, Electrically Powered Hand Prosthesis for Daily Living and Working," IEEE Robotics & Automation Magazine, pp. 87-101 (2017), 15 pages.
Piazza et al., "The SoftPro project: Synergy-based Open-source Technologies for Prosthetics and Rehabilitation," In: Carrozza et al. (eds) Wearable Robotics: Challenges and Trends. WeRob 2018. Biosystems & Biorobotics, vol. 22. Springer, Cham. (2018), 2 pages.
Piazza et al., "Toward and Adaptive Foot for Natural Walking," 2016 IEEE-RAS 16th Int'l Conf on Humanoid Robots (Humanoids), Cancun, Mexico, Nov. 15-17, 2016, pp. 1204-1210 (2016), 7 pages.
Santina et al., "The Quest for Natural Machine Motion: An Open Platform to Fast-Prototype Articulated Soft Robots," IEEE Robotics & Automation Magazine, pp. 2-11 (Mar. 2017), 10 pages.
Santina et al., "Toward Dexterous Manipulation with Augmented Adaptive Synergies: The Pisa/IIT SoftHand 2," IEEE Transactions on Robotics, vol. 34, No. 5, pp. 1141-1156 (2018), 16 pages.
Garcia Rodriguez, L., "Development of a fully flexure-based prosthetic hand," University of Twente, PDEng Thesis (2018), 90 pages.
Lee et al., "Tendon-Driven Compliant Prosthetic Wrist Consisting of Three Rows Based on the Concept of Tensegrity Structure," IEEE Robotics and Automation Letters, vol. 6, No. 2, pp. 3956-3963 (2021), 8 pages.

* cited by examiner

BIONIC JOINT AND A PROSTHESIS FOR REPLACING AN ELBOW JOINT

CROSS-REFERENCE TO RELATED APPLICATIONS

This application claims the benefit of European Patent Application No. 22201644.6, filed October 14, 2022, the disclosure of which is incorporated herein by reference in its entirety.

FIELD OF THE INVENTION

The present invention is in the field of prostheses. More precisely, the present invention relates to a prosthesis joint for replacing a joint in an upper body limb.

BACKGROUND

The upper extremities play an important role in everyday life and allow for fine and coordinated functions in prehensile, proprioceptive, and communication tasks. Compensating for the loss of upper extremities is still a technological and clinical challenge. Artificial limbs might help to restore some of the missing capabilities. However, there is still a wide gap between commercial devices and the requirements of prosthesis users in everyday life.

State-of-the-art commercial prostheses include simple passive cosmetic solutions or active devices. Cosmetic prostheses try to maximize self-acceptance and aesthetic value, but they generally do not offer any functional replacement, and may only allow specific joint adjustments using the contralateral hand. Active prostheses range from simple body-powered systems to electrically powered solutions, such as myoelectrically controlled prostheses using electromyography (EMG) sensors. Body-powered prostheses are very simple and operate by means of a cable control system that encompasses one or both shoulders and allows one control input. Myoelectric prostheses are designed to match the appearance and function of the upper limb through the use of actuators, batteries and sensors.

SU971312A1 teaches a prosthesis joint for an elbow joint and a knee joint with a rigid hinge. The prosthesis contains a reversible electric motor with an output shaft, a gearbox and a controllable prosthesis lever, wherein the gearbox is made in the form of parallel threads, with the ends attached to diametral points of the output shaft, wherein when the electric motor begins to rotate and transmits torque to the system of threads, the threads are twisted leading to a reduction in the length of the threads, to move the lever and drive a motion of the prosthesis around the joint.

WO 2011/028088 A1 discloses an elbow joint comprising a rigid hinge joint and a motor, wherein the motor is configured to drive a worm gear coupled to the hinge joint to drive a bending or extending rotation of the elbow joint.

SUMMARY OF THE INVENTION

Despite the technological development of the last decades, current solutions still present several limitations. For this reason, clinical and engineering research is actively investigating new strategies to improve the level of acceptability. Beyond replacing all the sensory-motor functions and the aesthetic appearance of the missing limb, other fundamental requirements are related to the reliability of the devices in everyday tasks and challenging situations.

Fundamental issues in the design of upper limb prostheses are the overall shape, dimensions, weight and performance of the system in real-life environments, e.g. in terms of robustness and safe interaction with the environment or other people. In addition, the relative orientation of the active DOFs with respect to the arm linkages should be designed to allow for a fluid and natural coordination of multiple joints.

In view of this state-of-the-art and the associated fundamental issues, the object of the invention is to provide a lightweight and functional artificial joint and prosthesis for upper body limbs, in particular the elbow, which is reliable in practice and allows for handling common tasks of the respective joint.

This object is solved by an artificial joint and prosthesis according to the independent claims. The dependent claims relate to preferred embodiments.

According to a first aspect, the invention relates to an artificial joint for a prosthesis or robot arm, the artificial joint comprising a first rigid link, a second rigid link, and a compliant joint rotatably connecting the first rigid link and the second rigid link with respect to a principal plane of rotation. The compliant joint comprises an elastic link extending between the first rigid link and the second rigid link, wherein rotating the first rigid link and the second rigid link with respect to each other in the principal plane of rotation deforms the elastic link. The artificial joint further comprises a first string section and a second string section both extending between the first rigid link and the second rigid link, being fixed to the second rigid link, and being arranged on opposite sides with respect to the compliant joint, such that shortening one of the first string section and of the second string section and lengthening the other one of the first string section and of the second string section drives a rotation of the first rigid link and the second rigid link with respect to each other in the principal plane of rotation.

The elastic link may mechanically connect the rigid links and may define an elastic hinge for relative rotation of the rigid links in the principal plane of rotation. The elastic link may enable a compliance of the artificial joint, such that an external force acting on the artificial joint may induce a relative movement of the first rigid link and the second rigid link to mirror a compliance inherent to natural limbs. The compliant joint may permit an out-of-plane rotation of the first rigid link and the second rigid link with respect to the principal plane of rotation, such as to enable motion often limited by common prosthesis harnesses, e.g. a humerus rotation for transhumeral elbow prostheses. Hence, the artificial joint may simplify a control of an associated prosthesis during common coordination tasks by reducing the rigidity of the driven prosthesis. Moreover, the artificial joint may allow for a more natural behavior and an increased level of comfort for the user. An additional benefit of this approach may be the possibility to absorb shocks, that can be especially beneficial for a patient with osseointegration, and that the artificial joint may enable a safe interaction with the environment and other people.

The first string section and the second string section may act as means for driving a rotation of the first rigid link and the second rigid link in the principal plane of rotation and can accommodate a compliant relative motion of the first rigid link and the second rigid link, such as torsion, out-of-plane rotation and/or relative translation. At the same time, the first string section and the second string section may reliably drive the rotation of the first rigid link and the second rigid link in the principal plane of rotation and may substantially maintain a relative angular orientation.

The first string section and the second string section may extend in or parallel to the principal plane of rotation for driving the rotation of the first rigid link and the second rigid link. The first string section and the second string section may be made of the same material and may be suitable to transmit a pulling force from the first rigid link on the second rigid link, such as to drive a relative rotation of the first rigid link and the second rigid link with respect to the compliant joint, which may act as a hinge for a bending motion. The first string section and the second string section should be flexible in a direction perpendicular to the direction along which the pulling forces are transmitted, such as to facilitate force transfer. For example, the first string section and the second string section may be made of metal and may extend between the first rigid link and the second rigid link in the form of cable strings.

Since the first string section and the second string section can maintain a compliance of the artificial joint in the out-of-plane direction (with respect to the principal plane of rotation) and/or for torsional movement of the first rigid link and the second rigid link, the resulting prosthesis may improve the level of acceptability, but may also support expected loads for an elbow joint during daily tasks, such as 4 kg or to kg for an elbow joint prosthesis, along the bending direction in the principal plane of rotation.

The first string section and the second string section may be concurrently driven to control a relative rotation of the rigid links, wherein the string sections may mimic antagonist muscles of a human joint. In some embodiments, the first string section and the second string section are coupled, e.g. mechanically coupled, such that a shortening of one of the string sections results in a lengthening of the other one of the string sections. For example, the string sections may be coupled to the same actuator, e.g. via opposite winding of the string sections on the same spindle.

In preferred embodiments, the compliant joint is compliant in an out-of-plane direction with respect to the principal plane of rotation.

The elastic link may be configured to define different effective elasticity coefficients for different relative motions of the first rigid link and the second rigid link, which may be based on the geometric arrangement and/or on the material choice for the elastic link. For example, the elastic link may comprise an elastic element extending between the first rigid link and the second rigid link and having different extension in a thickness direction in the principal plane of rotation and in a width direction in an out-of-plane direction with respect to the principal plane of rotation, such as to define different effective bending stiffness/flexural rigidity for a bending motion of the elastic element in the principal plane of rotation and in the out-of-plane direction.

In some embodiments, the elastic link is configured such that an external load to rotate the first rigid link and the second rigid link with respect to each other in the principal plane of rotation is smaller than an external load to rotate the first rigid link and the second rigid link with respect to each other in the out-of-plane direction and/or is smaller than an external load to twist the first rigid link and the second rigid link with respect to each other.

The skilled person will appreciate that the different effective elasticity coefficients of the elastic link and/or the different external loads for driving a relative motion of the first rigid link and the second rigid link against a restoring force of the elastic link may generally be defined with respect to a rest position of the artificial joint, wherein the rest position may be the position, to which the compliant joint is biased in the absence of external forces, e.g. due to the string sections. For example, the elastic link may not be deformed in the rest position, or internal restoring forces of the elastic link may cancel in the rest position.

Different bending stiffness/flexural rigidity of the artificial joint from a rest position may be implemented based on a selection and combination of materials of the elastic link as well as on the geometric arrangement and configuration of the elastic link. The elastic link may be made of a flexible material for enabling a bending motion of the first rigid link and the second rigid link. In principle, the elastic link may be made of a metal link which is configured to define a principal plane of rotation, such as by providing metal rods, strips or a sheet extending between the first rigid link and the second rigid link, whose geometric configuration may result in a lowest flexural rigidity for a hinged motion of the rigid links in the principal plane of rotation around the compliant joint. In preferred embodiments, the elastic link is made of a plastic material, e.g. PLA, and/or a (natural or artificial) rubber material, e.g. based on (thermoplastic) elastomers, such as thermoplastic polyurethane, thermoplastic rubber (TPR), or Thermoplastic Vulcanizate (TPV), such as to enable a sufficient compliance of the joint, which may be selected based on the joint in question and patient preference, e.g. through material and geometry selection for the elastic link. For example, an elbow joint may rotate in the out-of-plane direction by about 15° when the distal end of the corresponding prosthesis is subjected to a force smaller than 5 kg, such as between 0.1 kg and 5 kg, such as 0.5 kg, 1 kg, or 2 kg.

In preferred embodiments, the elastic link comprises a first elastic element, and a second elastic element, wherein the first elastic element and the second elastic element each extend between the first rigid link and the second rigid link, and rotating the first rigid link and the second rigid link with respect to each other in the principal plane of rotation deforms the first elastic element and the second elastic element.

Using two elastic elements for defining the elastic link can facilitate the assembly as well as the design of the compliant joint with respect to different intended bending stiffness for different relative movements of the first rigid link and the second rigid link.

In preferred embodiments, the first elastic element and the second elastic element are offset from each other along the normal of the principal plane of rotation.

The normal is generally understood as the vector which is perpendicular to the corresponding plane and points out of the principal plane of rotation. Preferably, the first elastic element and the second elastic element are spaced along the normal of the principal plane of rotation. In some embodiments, the first elastic element and the second elastic element are symmetric with respect to the principal plane of rotation.

The rotation of the first rigid link and the second rigid link in the principal plane of rotation may induce a symmetric bending of the first elastic element and the second elastic element. On the other hand, a torsional motion or out-of-plane rotation of the first rigid link and the second rigid link may induce a lengthening/compression and/or shearing forces in the first elastic element and the second elastic element, such that suitable resistance to such relative movements can be implemented by tuning the respective effective coefficients of elasticity of the first elastic element and the second elastic element, e.g. based on the material selection and/or the geometry of the elastic elements, and/or by selecting a suitable spacing of the elastic elements.

In preferred embodiments, the first string section and the second string section are arranged between the first elastic element and the second elastic element.

With the first string section and the second string section being arranged between the elastic elements, a pulling force exerted by one of the string sections may be equally distributed to the elastic elements, which may bend in a symmetric manner, such as to enable a driven rotation of the compliant joint.

The elastic elements may define an internal joint space between each other along the normal of the principal plane of rotation and the first string section and the second string section can be arranged between the first elastic element and the second elastic element along the normal of the principal plane of rotation within or next to the internal joint space. Accordingly, the first string section and the second string section can be free to move into the internal joint space between the first elastic element and the second elastic element, and may not interfere with the elastic link, as the elastic elements are deformed as part of a rotation of the rigid links in the principal plane of rotation.

Preferably, the first string section and the second string section lie in and define the principal plane of rotation, and the first elastic element and the second elastic element are arranged on opposite sides of the principal plane of rotation and are spaced form each other along the normal of the principal plane of projection.

The configuration of the first elastic element and the second elastic element may be adapted to define a suitable flexural rigidity of the resulting elastic link. For example, each of the first elastic element and the second elastic element may be configured as a flexural hinge, which may feature a lowest effective thickness in the principal plane of rotation in its middle section, such as to promote a hinging motion at which the flexural hinge is bent close to its middle link section. A thickness of the first elastic element and the second elastic element at a middle section of the artificial joint may be smaller than a width of the first elastic element and the second elastic element in the out-of-plane direction. The elastic elements may be made of a flexible material, which may be a (natural or artificial) rubber material, e.g. based on elastomers, such as thermoplastic polyurethane.

In preferred embodiments, the first elastic element and the second elastic element are implemented as a cross-flexural hinge defining a hinged connection for rotation of the first rigid link and the second rigid link in the principal plane of rotation.

The cross-flexural hinge may be implemented with simple technical means and provides a plurality of design parameters to adapt the artificial joint to different joints and/or patients.

The cross-flexural hinge may be implemented by providing crossed bars of a flexible material for the first elastic element and for the second elastic element, such that a cross-flexural hinge may be arranged on each side of the principal plane of rotation.

However, any number of crossed bars may be used in embodiments, such as by implementing to the cross-flexural hinge with two first elastic bars with a first orientation, which may be arranged on opposite sides of the principal plane of rotation and a second elastic bar at or close to the principal plane of rotation, which has a different orientation, such that the second elastic bar may cross the first elastic bars, when viewed along the normal of the principal plane of rotation.

In preferred embodiments, each of the first elastic element and the second elastic element comprises a first elastic bar and a second elastic bar extending between the first rigid link and the second rigid link, wherein the first elastic bar and the second elastic bar cross each other, when viewed along the normal of the principal plane of rotation.

The flexible bars may be understood as linkages of a flexible material whose main extension direction extends between the rigid links. The flexible bars may be beam- or rod-shaped in some embodiments, but in general need not follow a strict geometric shape. The flexible bars may have their opposite ends fixed to the first rigid link and the second rigid link, such as to extend between and connect the rigid links. In preferred embodiments, the flexible material of the elastic bars is a rubber material, which may be based on elastomers, such as thermoplastic polyurethane, and may in particular be a 3D-printable elastomer.

The cross-flexural hinges based on the flexible bars may provide desirable characteristics for the artificial joint with respect to compliance of the artificial joint in the out-of-plane direction and with respect to torsional movement of the rigid links, wherein a flexural rigidity with respect to an intended relative rotation of the rigid links in the principal plane of rotation around the compliant joint can be comparatively low over a large range of angular motion, e.g. larger than 90° or larger than 120°, with respect to relative torsional/out-of-plane movement or relative translation.

To enable a large angular range of motion of the compliant joint, the elastic link preferably defines a rest position of the compliant joint between extremal angular positions from which the elastic link resists external loads based on a corresponding deformation of the elastic link required to drive a relative motion of the rigid links with respect to the compliant joint.

In preferred embodiments, the elastic link is configured to bias the first rigid link and the second rigid link towards a rest position, in which the first rigid link and the second rigid link are at a predefined rest angle to each other, wherein the predefined rest angle is in particular between 30° and 150°, preferably between 45° and 135° or between 60° and 100°, and/or wherein the predefined rest angle is selected from an angular interval between 25% and 75% of the angular range of motion of the artificial joint in the principal plane of rotation.

The rest angle may be defined between the rigid links in the principal plane of rotation and may be an intermediate angle with respect to an intended angular range of motion of the compliant joint, such as a rest angle of 90° for an angular range of motion between 0° (fully extended) and 135° or 150° (maximum bend angle), e.g. for an elbow joint.

From the rest angle, the rigid links may be rotated with respect to each other by driving a respective shortening/lengthening of the string sections, which are preferably both arranged in the principal plane of rotation.

The first string section and the second string section may be actively driven, e.g. by an electromotor associated with the prosthesis, or may be coupled to an external actuator, e.g. to be directly driven by the patient as a body-powered prosthesis. For example, the first string section and the second string section of the artificial joint may be coupled to attachment points on one or both shoulders to drive a relative rotation of the lower and upper arm for an elbow joint prosthesis. In some examples, the prosthesis is implemented as a passive prosthesis, wherein a control element of the prosthesis may be actuated by the contralateral hand of the patient, such as to adjust a relative length of the first string section and the second string section. The prosthesis may comprise a locking mechanism, e.g. a mechanical switch, for locking a current configuration of the string sections, such as to manually lock the position of the artificial joint in a certain position.

In preferred embodiments, the artificial joint further comprises an electric motor configured to drive a shortening of the first string section and/or of the second string section to drive the rotation of the first rigid link and the second rigid link with respect to each other in the principal plane of rotation.

The electric motor may be arranged in the first rigid link and preferably acts on both of the string sections, e.g. through a coupling of the string sections to each other.

For example, the shortening/lengthening of first string section and the second string section may be coupled, such that a shortening of the first string section is coupled to a lengthening of the second string section, and vice-versa. Thus, an angular position of the rigid links can be maintained in both directions as the rigid links are rotated in the principal plane of rotation with respect to the compliant joint.

In preferred embodiments, the artificial joint further comprises a spindle arranged in the first rigid link and coupled to a first pulley and a second pulley connected to the first string section and the second string section, respectively, such that rotating the spindle winds up one of the first string section and of the second string section on the respective one of the first pulley and the second pulley and unwinds the other one of the first string section and of the second string section from the respective other one of the first pulley and the second pulley, for driving a rotation of the first rigid link and the second rigid link with respect to each other around the compliant joint.

The string sections can be fixedly connected to the pulleys, and the pulleys may be configured as reels for winding up the string sections on the respective pulleys. The pulleys may be arranged on the spindle and may be rotatably fixed to the spindle at different positions. The spindle may couple a length of the first string section and of the second string section extending between the rigid links, and may define a pair of string lengths for the first string section and the second string section as the rigid links are rotated in the principal plane of rotation with respect to the compliant joint. The pulleys may comprise a groove between radially protruding flanges, such as to define reception spaces for winding up the respective string sections. The pulleys may be integrally formed in the spindle, such that the string sections may be effectively wound up on different sections of the spindle.

The spindle may be coupled to the electric motor arranged in the first rigid link, e.g. by coupling the spindle to the rotor of the electric motor, preferably via a gearbox, such as to define a suitable force transmission and/or to enable a locking of a current angular position of the compliant joint by selectively preventing a rotation of the spindle, or based on a passive stall torque of the electric motor.

The first rigid link may be a proximal prosthesis part of the artificial joint, such as to move a weight of the driving assembly of the string sections, which may include the spindle and/or the motor, closer to the body of the patient.

The spindle may be arranged to extend perpendicular to the main axis of the first rigid link, e.g. such that the spindle may extend perpendicularly to the direction along which the first rigid link is spaced from the compliant joint. Thus, the string sections may extend perpendicular to the spindle, and rotating the spindle may drive a rotation of the rigid links around the compliant joint.

Preferably, the spindle extends substantially along the main axis of the first rigid link and the first string section and the second string section are deflected at the first rigid link, such as to extend substantially perpendicular to the spindle axis towards the spindle from respective points of deflection.

In preferred embodiments, the artificial joint further comprises a first bearing and a second bearing mounted on opposite sides of the first rigid link in the principal plane of rotation, the first bearing and the second bearing being configured to receive the first string section and the second string section, respectively, extending from the second rigid link towards the first rigid link.

The first bearing may receive the first string section and may guide the first string section towards the first pulley. Similarly, the second bearing may receive the second string section and may guide the second string section towards the second pulley.

In preferred embodiments, the first bearing and the second bearing are spaced along an axis of the spindle with respect to each other in accordance with a spacing of the first pulley and the second pulley along the spindle.

Accordingly, a risk of interference of the first string section and the second string section at or close to the spindle may be reduced, and a reliability of the mechanism may be increased.

Preferably, the bearings are spaced along the axis of the spindle according to a range of motion of the artificial joint from a rest position. For example, if the rest position is not symmetric with respect to an intended angular range of motion of the rigid links around the compliant joint, then the bearing of the string section, which is associated with a larger range of shortening from the rest position to an extremal point of the angular range, is spaced farther from the compliant joint along the spindle axis than the other bearing.

For example, when the artificial joint is an elbow joint with an intended angular range of motion between 0° (fully extended) and about 130° (maximally bent) as well as a rest position of the elastic link at about 90°, the dorsal bearing may be spaced farther from the compliant joint than the ventral bearing, such as to accommodate a larger angular range of motion for extending the artificial joint towards the fully extended configuration (0°) for which the dorsal string section is shortened.

Similarly, an attachment geometry of the first string section and the second string section may be adapted to asymmetric ranges of angular motion of the rigid links in the principal plane of rotation in opposite directions from the rest position. For example, a mounting support of the second rigid link may be adapted to receive the first string section and the second string section and may fixedly connect the string sections to the second rigid link. In the rest position, the mounting support may receive the first string section and the second string section at different distances from a center of the compliant joint, in particular at different distances along a spacing direction along which the first rigid link and the second rigid link are spaced.

The distance of the point from the compliant joint, at which the first string section is received, may be larger for the string section, which is associated with a larger range of shortening from the rest position to an extremal point of the angular range.

In some embodiments, the first string section and the second string section are attached to the second rigid link at respective mounting positions, wherein the respective mounting positions are on a side of the second rigid link, which is opposite to a side facing the first rigid link.

For example, the string sections may be received on the mounting support of the second rigid link and curve around an outer surface of the mounting support to a mounting side of the mounting support, which is opposite to a side facing the first rigid link.

As a result, a spatial footprint of the compliant joint may be reduced by mounting the string sections within a framework of the second rigid link. Further, attaching the string sections at said opposite side may prevent fasteners for attaching the string sections to the second rigid link from protruding from the framework of the second rigid link in the principal plane of rotation, such that a reliability and level of acceptance of a prosthesis can be increased.

In some embodiments, the mounting support is slanted with respect to the spacing direction of the rigid links, such as to minimize a material use/weight of the artificial joint while accommodating asymmetric ranges of angular motion in the principal plane of rotation from the rest position.

In preferred embodiments, the first rigid link and the second rigid link are rotatably connected over a pre-determined range of angular motion, wherein the second rigid link comprises a first channel and second channel for guiding the first string section and the second string section, respectively, to respective mounting positions, wherein the respective mounting positions are on a side of the second rigid link, which is opposite to a side facing the first rigid link.

Said channels may prevent sideways deflection of the string sections in the presence of external forces acting on the artificial joint, such that a reliability of the artificial joint may be increased. Moreover, the channels may be compatible with the compliant joint, wherein the channels may accommodate longer or shorter segments of the string sections, depending on a dynamic relative movement of the rigid links in the principal plane of rotation, which need not correspond to a perfectly circular hinged motion around the center of the compliant joint. The channels may be formed in a curved surface of the mounting support, which may curve around the mounting support to said mounting side of the mounting support. As a result, the rotation of the rigid links around the compliant joint may be reliably driven over a large angular range of motion using the string sections.

The artificial joint can form part of a prosthesis to provide a compliant prosthesis whose joint angle can be changed and fixed over a large angular range of motion, in particular in an actively driven prosthesis with an internal motor or in a body powered prosthesis. The skilled person will however appreciate that the artificial joint being suitable for a prosthesis may equally be suitable for use in a robot, in particular in a robot intended for executing human tasks, which may benefit from a compliance of the corresponding robotic manipulator, e.g. a robot arm during coordination tasks.

In preferred embodiments, the artificial joint of any one of the preceding embodiments is a joint of a prosthesis for replacing a joint of an upper body extremity, in particular for replacing an elbow joint, and the first aspect relates to the prosthesis.

Generally, the prosthesis may be a full prosthesis, such as a transhumeral prosthesis for replacing a missing lower arm and a part of an upper arm, or may be a (prosthesis) part of a composite prosthesis, which may e.g. attach to an upper arm prosthesis attachment, such as a shoulder/upper arm harness or a mounting part connected to a bone of a patient, and which may also feature a mounting portion for receiving a lower arm prosthesis.

In preferred embodiments, the first rigid link is a proximal prosthesis part and the second rigid link is a distal prosthesis part.

For example, the first rigid link may be configured as an upper arm prosthesis or a distal end thereof, and the second rigid link may be configured as a lower arm prosthesis or a proximal end thereof. As a result, the string sections may be ventral and dorsal string sections arranged on opposite sides of an effective hinge location of the compliant joint in the principal plane of rotation.

According to a second aspect, the invention relates to a prosthesis, the prosthesis comprising a first rigid link, a second rigid link, and a joint arranged between an end of the first rigid link and an end of the second rigid link and configured to enable a rotational movement between the first rigid link and the second rigid link with respect to each other. The prosthesis further comprises a first string section and a second string section extending from the first rigid link to the second rigid link, being both fixed to the second rigid link, and arranged on opposite sides of the joint, and a spindle arranged in the first rigid link and coupled to a first pulley and a second pulley connected to the first string section and the second string section, respectively, such that rotating the spindle winds up one of the first string section and of the second string section on the respective one of the first pulley and the second pulley and unwinds the other one of the first string section and of the second string section from the respective other one of the first pulley and the second pulley, for driving a rotation of the first rigid link and the second rigid link with respect to each other around the joint.

The prosthesis may be configured for replacing an upper body limb and may comprise a joint defining a hinged connection between the rigid links. The joint may be a conventional hinge joint, such as to implement a load-bearing joint of a foot or a knee, but preferably is an elastic joint, e.g. for capitalizing on a compatibility of the driving mechanism using string sections with a non-rigid hinge connection between the rigid links, which may be advantageously used in upper body limbs.

In preferred embodiments, the prosthesis further comprises an electric motor configured to drive a shortening of the first string section and/or of the second string section to drive the rotation of the first rigid link and the second rigid link with respect to each other in the principal plane of rotation, wherein the electric motor is in particular arranged in the first rigid link and configured to drive a rotation of the spindle.

In preferred embodiments, first rigid link is configured as an upper arm prosthesis or part thereof, wherein the end of the first rigid link corresponds to a distal portion of the humerus, and the second rigid link configured as a lower arm prosthesis or part thereof and the end of the second rigid link corresponds to a proximal portion of the ulna and radius.

In preferred embodiments, the first string section is a ventral string section and the second string section is a dorsal string section.

In preferred embodiments, the prosthesis further comprises a first bearing and a second bearing mounted on opposite sides of the first rigid link in the principal plane of rotation, the first bearing and the second bearing being configured to receive the first string section and the second string section, respectively, extending from the second rigid link towards the first rigid link.

In preferred embodiments, the first bearing and the second bearing are spaced along an axis of the spindle with respect to each other in accordance with a spacing of the first pulley and the second pulley along the spindle.

In preferred embodiments, the second rigid link comprises a ventral first channel and dorsal second channel for guiding the first string section and the second string section to respective mounting positions, wherein the respective mounting positions are on a side of the second rigid link, which is opposite to a side facing the first rigid link.

In preferred embodiments, the joint is a compliant joint and the prosthesis comprises an artificial joint of any embodiment of the first aspect.

In some embodiments, a gearbox is arranged in the first rigid link coupled between the spindle and the electric motor.

In some embodiments, a circuit board is arranged in the first rigid link and configured to control the electric motor.

According to a third aspect, the invention relates to a passive joint prosthesis comprising a first rigid link, a second rigid link, and a pair of cross-flexural pivots extending between the first rigid link and the second rigid link for defining a cross-flexural hinge with a principal plane of rotation, the cross-flexural pivots being spaced along the normal of the principal plane of rotation from each other. Each of the cross-flexural pivots comprises a first elastic bar and a second elastic bar extending between the first rigid link and the second rigid link, wherein the first elastic bar and the second elastic bar cross each other, when viewed along the normal of the principal plane of rotation. The passive prosthesis further comprises a locking mechanism for selectively restraining a rotation of the first rigid link with respect to the second rigid link in the principal plane of rotation.

DETAILED DESCRIPTION OF EMBODIMENTS

The features and numerous advantages of the devices according to the present invention will best be understood from a detailed description of preferred embodiments with reference to the accompanying drawings, in which:

FIG. 1A-1C schematically illustrate an artificial joint for a prosthesis according to three example configurations;

Figure 1A:
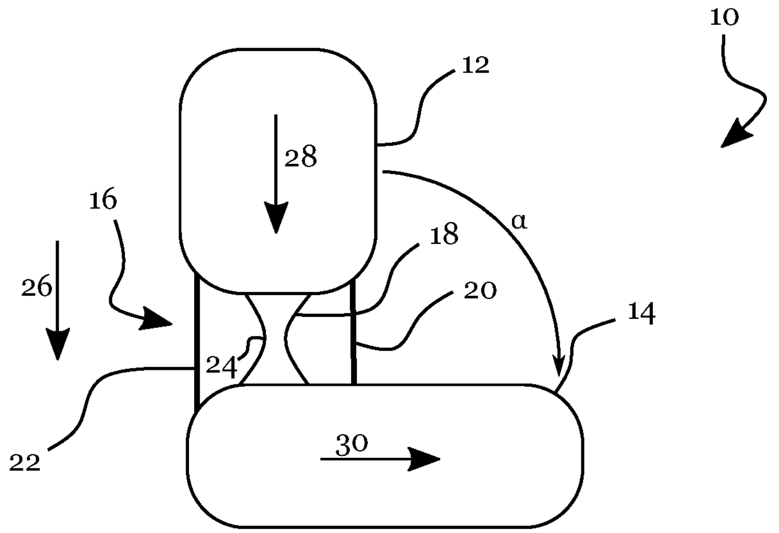
Figure 1B:
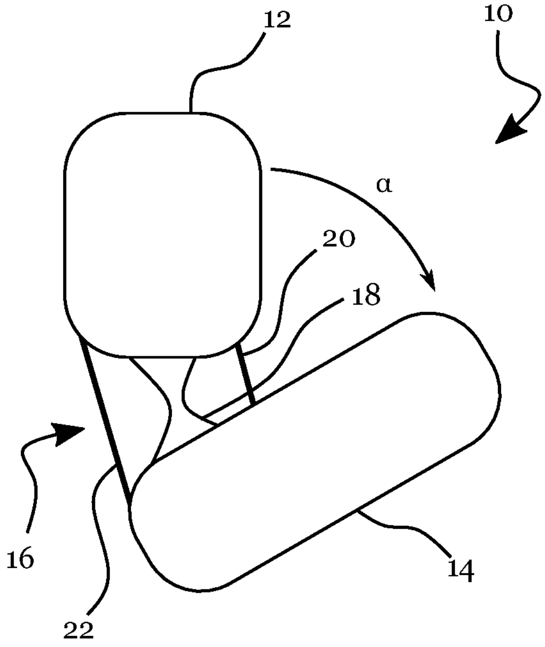
Figure 1C:
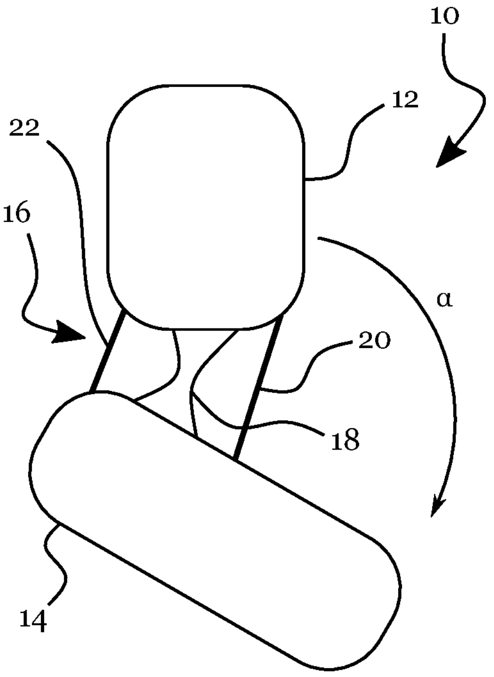

FIGS. 1A-C schematically illustrate an artificial joint to for a prosthesis according to three example configurations. The artificial joint to comprises a first rigid link 12, a second rigid link 14, and a compliant joint 16 rotatably connecting the first rigid link 12 and the second rigid link 14 with respect to a principal plane of rotation, which coincides with the plane of projection in FIGS. 1A-C. The compliant joint 16 comprises an elastic link 18 extending between the first rigid link 12 and the second rigid link 14. The artificial joint to further comprises a first string section 20 and a second string section 22, which extend between the first rigid link 12 and the second rigid link 14 on opposite sides of the compliant joint 16.

The elastic link 18 extending between the first rigid link 12 and the second rigid link 14 is deformable and enables a relative movement of the first rigid link 12 and the second rigid link 14 around the compliant joint 16 effectively acting as a hinge. As shown in FIGS. 1A-1C, the elastic link 18 may have a tapered cross-section, when looking onto the principal plane of rotation (plane of projection in FIGS. 1A-1C), and may feature wider fillet sections close to the rigid links 12, 14 which may taper towards a middle section 24, such that a thickness of the middle section 24 in the principal plane of rotation may be smaller than a thickness of the elastic link 18 closer to the rigid links 12, 14.

One end of each of the string sections 20, 22 is fixed to the second rigid link 14, and the respective other end can be received at the first rigid link 12 in a slidable manner, e.g. at a bearing (not shown) mounted in the first rigid link 12, such that the string sections 20, 22 extending from the second rigid link 14 can be pulled into the first rigid link 12.

In FIG. 1A, the compliant joint 16 is in its rest position, wherein the elastic link 18 does not bias the rigid links 12, 14 out of its current position and is substantially free from deformation. The compliant joint 16 spaces the rigid links 12, 14 along a spacing direction 26, and the rigid links 12, 14 extend from the compliant joint 16 along respective main axes 28, 30, which may correspond to the main extension directions of the bones replaced by the prosthesis. In FIG. 1A, an angle α between the first rigid link 12 and the second rigid link 14 is substantially 90°, with respect to the main axes 28, 30 of the rigid links 12, 14.

It is noted that, in the following, a convention adopted in this disclosure is that the angle between two prosthesis parts is zero, when the joint is in its fully extended configuration, i.e. that opposite ends of the rigid links are farthest from each other, and their main axes 28, 30 are parallel, as opposed to a convention in which the angle would be zero when the rigid links are folded towards each other until they are parallel. Thus, when reference is made to the bending angle of the artificial joint to in the following, the angle is effectively 180°-a.

In the illustrated example, a rotation of the first rigid link 12 and the second rigid link 14 with respect to each other in the principal plane of rotation can be driven by shortening one of the first string section 20 and of the second string section 22 and lengthening the other one of the first string section 20 and of the second string section 22.

In the example of FIG. 1B, the first string section 20 is shortened and the second string section 22 is lengthened concurrently, such that the angle α between the first rigid link 12 and the second rigid link 14 is reduced, corresponding to an increase of the bending angle of the artificial joint to.

Conversely, in the example of FIG. 1C, the first string section 20 is lengthened and the second string section 22 is shortened concurrently, such that the angle α between the first rigid link 12 and the second rigid link 14 is increased, corresponding to a reduction of the bending angle of the artificial joint to.

Thus, the bending angle of the artificial joint to in the principal plane of rotation may be actively controlled by pulling on one of the string sections 20, 22 from the first rigid link 12 and relaxing the respective other one of the string sections 20, 22. The respective string sections 20, 22 may be pulled by an electric motor in the prosthesis, an external actuator, or may be powered by a patient, e.g. by actuating a corresponding control element on the prosthesis or by routing the string sections 20, 22 as cables to a suitable harness for implementing a body-powered prosthesis joint.

A rest angle 180°-α may be selected in embodiments depending on the joint to be replaced, in particular based on a range of angular motion supported by the artificial joint to in the respective application. A rest angle of 90°, as shown in FIG. 1A, may be suitable for an elbow prosthesis joint which may typically move between an angle of 0° (fully extended) and 150° (approx. natural human limit) or a subset thereof, such as between approximately 20° and approximately 130°. Selecting a rest angle in a subset of the supported angular range of motion, such as a value in an angular interval between 70% and 30% of the angular range of motion may reduce strain on the elastic link 18, when the compliant joint 16 is deformed towards the extreme angles of the supported angular range of motion, and may introduce a restoring force towards the rest angle, which may be a commonly assumed angle for the respective joint.

Preferably, the elastic link 18 substantially extends over the width of the artificial joint to along a normal direction of the principal plane of rotation, such as to increase a flexural rigidity of the compliant joint 16 against relative movement of the rigid links 12, 14, which is not a rotation in the principal plane of rotation. The width of the elastic link 18 along the normal direction may be more than twice, in particular more than four times the thickness of the elastic link 18 at its middle section 24. For example, the elastic link 18 may comprise two elastic elements, which may be spaced along the normal direction of the principal plane of rotation on opposite sides of the artificial joint to, such as to define a large effective width of the elastic link 18.

Figure 2:
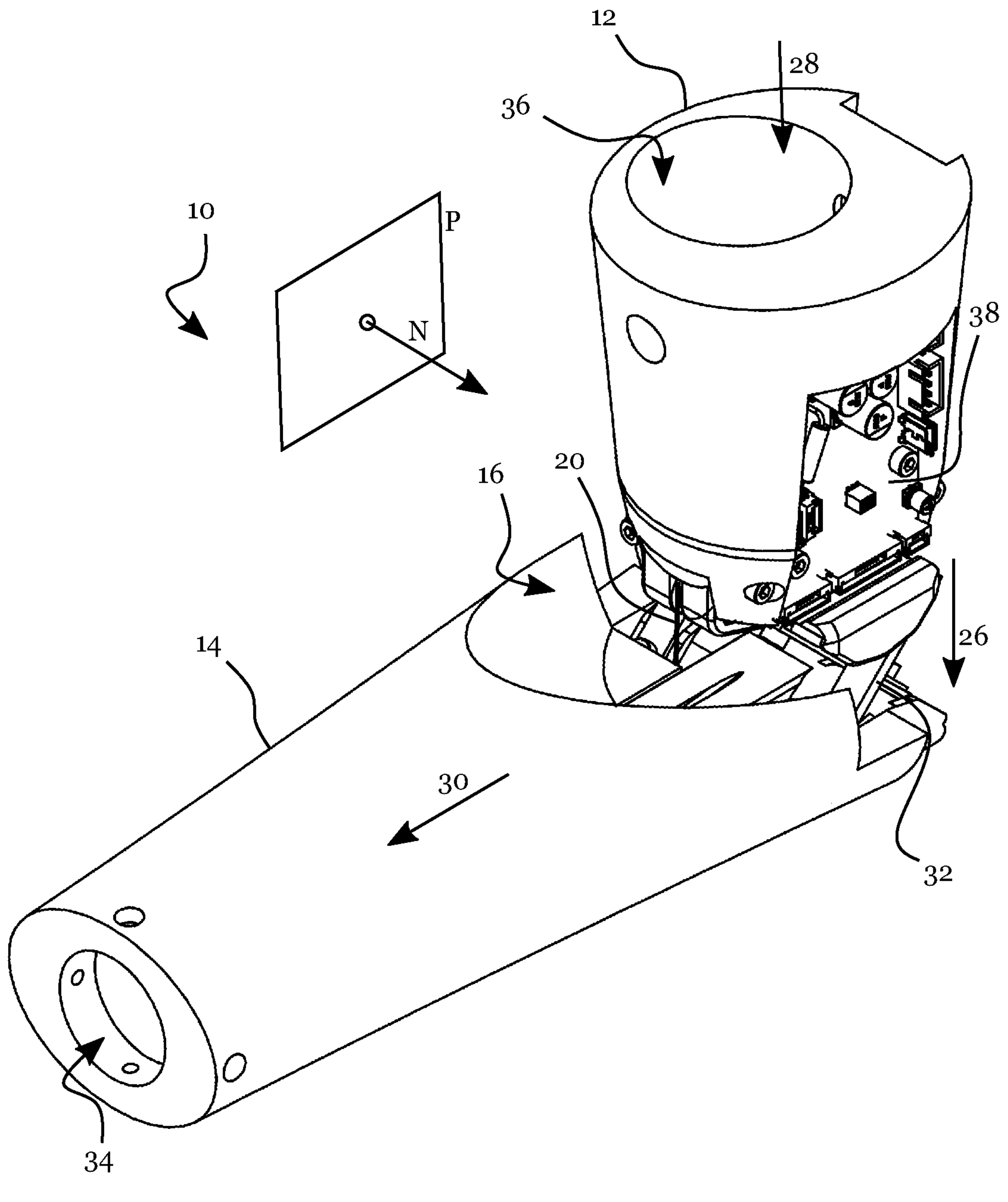
FIG. 2 illustrates another example of an artificial joint suitable for replacing a human elbow joint as an elbow joint prosthesis.

FIG. 2 illustrates another example of an artificial joint to suitable for replacing a human elbow joint as an elbow joint prosthesis. The artificial joint to comprises a first rigid link 12 and a second rigid link 14 connected via a compliant joint 16, which comprises a cross-flexural hinge 32 as an elastic link 18 extending between the first rigid link 12 and the second rigid link 14 along the spacing direction 26. A first string section 20 and a second string section (not shown in FIG. 2) extend on opposite sides of the compliant joint 16 for driving a relative rotation of the rigid links 12, 14 in the principal plane of rotation P which may be spanned by the main axes 28, 30 of the rigid links 12, 14.

The first rigid link 12 is configured as a distal portion of an upper arm prosthesis and the second rigid link 14 is configured as a proximal portion of a lower arm prosthesis. As illustrated in FIG. 2, the second rigid link 14 may comprise a mounting section 34 for a wrist prosthesis at its distal side and the first rigid link 12 may comprise a mounting section 36 at its proximal side for attaching the prosthesis to a suitable mount at an upper arm of a patient.

The first string section 20 is configured to lie at a ventral side of the elbow joint prosthesis for increasing a flexion (bending angle) of the elbow joint prosthesis, when the first string section 20 is shortened. The second string section 22 is configured to lie at a dorsal side of the elbow joint prosthesis for reducing a flexion of the elbow joint prosthesis and extending the lower arm from the upper arm, when the second string section 22 is shortened.

One end of each of the string sections 20, 22 may be fixedly attached at the second rigid link 14 and the respective shortening/lengthening of the first string section 20 and the second string section 22 may be driven by an electric motor (not shown in FIG. 2) located in the first rigid link 12, which may pull the respective string section 20, 22. However, the arrangement may in principle be opposite, i.e. the string sections 20, 22 may be fixed to the proximal first rigid link 12 and may be pulled into/relaxed from the distal second rigid link 14, in some embodiments.

If the artificial joint to is actively driven with an electric motor, a circuit board 38 may be mounted in the rigid links 12, 14 to control the electric motor. The circuit board 38 may be used to interpret myoelectric signals sensed from a patient as a control input or may receive control signals for driving the rotation of the artificial joint to via the string sections 20, 22.

Figure 3:
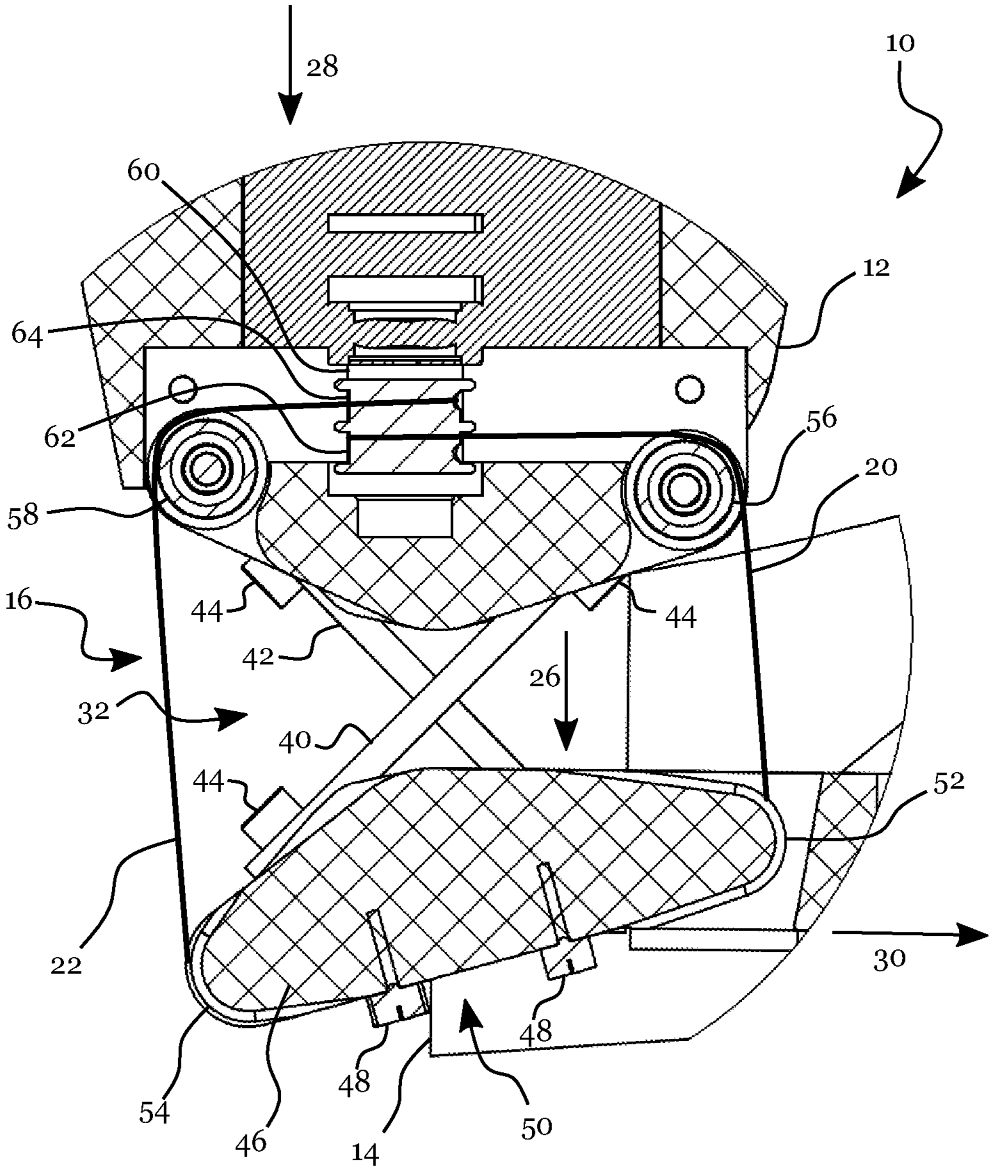
FIG. 3 illustrates a sectional sideview of an example of an artificial joint in its rest position.

FIG. 3 illustrates a sectional sideview of an example of an artificial joint to in its rest position, which may be a detail view of the artificial joint to of the example in FIG. 2. The artificial joint 10 comprises a first rigid link 12, a second rigid link 14 and a compliant joint 16 comprising a cross-flexural hinge 32 as an elastic link 18 extending between and connecting the first rigid link 12 and the second rigid link 14 along a spacing direction 26 of the compliant joint 16.

The cross-flexural hinge 32 comprises a first elastic bar 40 and a second elastic bar 42 each extending between the first rigid link 12 and the second rigid link 14 and attached to the rigid links 12, 14 at respective opposite sides via fasteners 44. The elastic bars 40, 42 can be made of a flexible rubber-like material, such as thermoplastic polyurethane, and cross each other, when viewed along the normal N of the principal plane of rotation P to form a cross-flexural pivot. In some embodiments a cross-flexural pivot may be provided on each side of the compliant joint 16 with respect to the normal direction N, such as to form a composite cross-flexural hinge 32 with two cross-flexural pivots as first and second elastic elements spaced along the width direction of the compliant joint 16.

The cross-flexural hinge 32 may be constructed from simple geometric shapes of the elastic rubber-like material and may naturally feature a tapered middle section 24 with comparatively low thickness, such that a pivot point of the associated compliant joint 16 may be well defined.

A first string section 20 and a second string section 22 may be arranged between the cross-flexural pivots formed by the elastic bars 40, 42 and may be located in a center of the cross-flexural hinge 32 with respect to the normal direction N. As illustrated in FIG. 3, the string sections 20, 22 may be arranged on opposite sides of the compliant joint 16 in the principal plane of rotation P to drive opposite rotations of the artificial joint to.

The string sections 20, 22 are each fixedly attached at a mounting support 46 of the second rigid link 14 via fasteners 48 at a mounting side 50, which is opposite to a side which faces the first rigid link 12. From the respective mounting positions at the fasteners 48, the string sections 20, 22 run over respective curved surfaces 52, 54 at opposite sides of the mounting support 46, with respect to a direction in the principal plane of rotation P, which is perpendicular to the spacing direction 26. The curved surfaces 52, 54 guide the string sections 20, 22 from the mounting side 50 towards a space between the rigid links 12, 14. From the respective curved surfaces 52, 54, the string sections 20, 22 extend towards respective bearings 56, 58 mounted at opposite sides of the first rigid link 12, with respect to a direction in the principal plane of rotation P, which is perpendicular to the spacing direction 26.

The bearings 56, 58 slidably receive the string sections 20, 22 and can each deflect the string sections 20, 22 towards a spindle 60 mounted in the first rigid link 12 between the two bearings 56, 58. A first pulley 62 and a second pulley 64 are rotatably fixed to the spindle 60 and are configured to receive the first string section 20 and the second string section 22, respectively.

The string sections 20, 22 may be fixedly attached to the respective pulley 62, 64, such that rotating the spindle 60 winds up/unwinds the string sections 20, 22 on/from the respective pulley 62, 64. The pulleys 62, 64 may each define respective reception spaces for holding a portion of the respective string section 20, 22, as the string sections 20, 22 are wound up/unwound by rotating the spindle 60. The first string section 20 and the second string section 22 may be wound on the respective pulley 62, 64 in opposite winding directions, such that rotating the spindle 60 concurrently winds up one of the first string section 20 and the second string section 22 and unwinds the other one of the first string section 20 and the second string section 22. Thus, by driving a rotation of the spindle 60, one of the first string section 20 and the second string section 22 extending between the rigid links 12, 14 is effectively shortened and the other one of the first string section 20 and the second string section 22 extending between the rigid links 12, 14 is effectively lengthened, such that a rotation of the spindle 60 can drive a rotation of the artificial joint to.

As illustrated in FIG. 3, the pulleys 62, 64 may be spaced along the spindle axis, and the bearings 56, 58 may be offset according to the spacing of the pulleys 62, 64, such that the string sections 20, 22 may be deflected towards the respective pulley 62, 64 at angle, which is substantially perpendicular to the spindle axis.

Preferably, the bearing 58, which is associated with the string section 22 subjected to a larger shortening for supporting an intended range of angular motion of the artificial joint to from its rest position, is spaced farther from the second rigid link 14 than the other bearing 56. For example, for a rest angle of 90° for an elbow joint prosthesis, which should provide an angular range of about 0° (fully extended) to about 135° (fully bent), in accordance with the illustrated example, the dorsal (i.e. the second) string section 22 may be shortened by a larger distance than the ventral (i.e. the first) string section 20. Thus, the dorsal second bearing 58 may be spaced farther from the second rigid link 14 along the spindle axis than the ventral first bearing 56 in the rest position.

The skilled person will appreciate that the pulleys 62, 64 can be integrally formed with each other (as shown in the example of FIG. 3) and/or with the spindle 60, or may be separate pulleys 62, 64 which are rotatably coupled to the spindle 60 or are attached to the spindle 60 in a rotatably fixed manner. As an example, the pulleys 62, 64 may be defined by a radially protruding separation formed in or mounted on the spindle 60, such as to separate different portions of the spindle 60 into respective first and second pulleys 62, 64.

The skilled person will further appreciate that, although the string sections 20, 22 may be different strings, in some embodiments, the string sections 20, 22 may be implemented by one cable string, which may run around the mounting support 46, e.g. in a suitable groove or channel, and may be fixed at one point of the mounting support 46, such as to prevent relative motion of the cable string and the mounting support 46. The mounting support 46 may be a portion of the second rigid link 14 or may be a separate part, which can be fixedly attached to a framework of the second rigid link 14 and which may be made of a different material than outer portions of the framework, such as to increase a rigidity of the mounting support 46.

The string sections 20, 22 may be received at the second rigid link 14 at different distances along the spacing direction 26. The different distances at which the string sections 20, 22 are received may accommodate asymmetric ranges of angular motion in the principal plane of rotation P from the rest position.

For example, the mounting support 46 may be effectively slanted, such that the string sections 20, 22 are received at different distances from a center of the compliant joint 16 and/or the first rigid link 12, as illustrated in FIG. 3. The mounting support 46 may be substantially bar shaped, such that a normal direction of the mounting side 50 may effectively be at angle with respect to the spacing direction 26, e.g. to minimize a material use/weight of the artificial joint to. However, the string sections 20, 22 may equally be received at separate mounts, such as being fixed to different pins of the second rigid link 14, which may extend along the normal direction N inside of the framework of the second rigid link 14.

Figure 4:
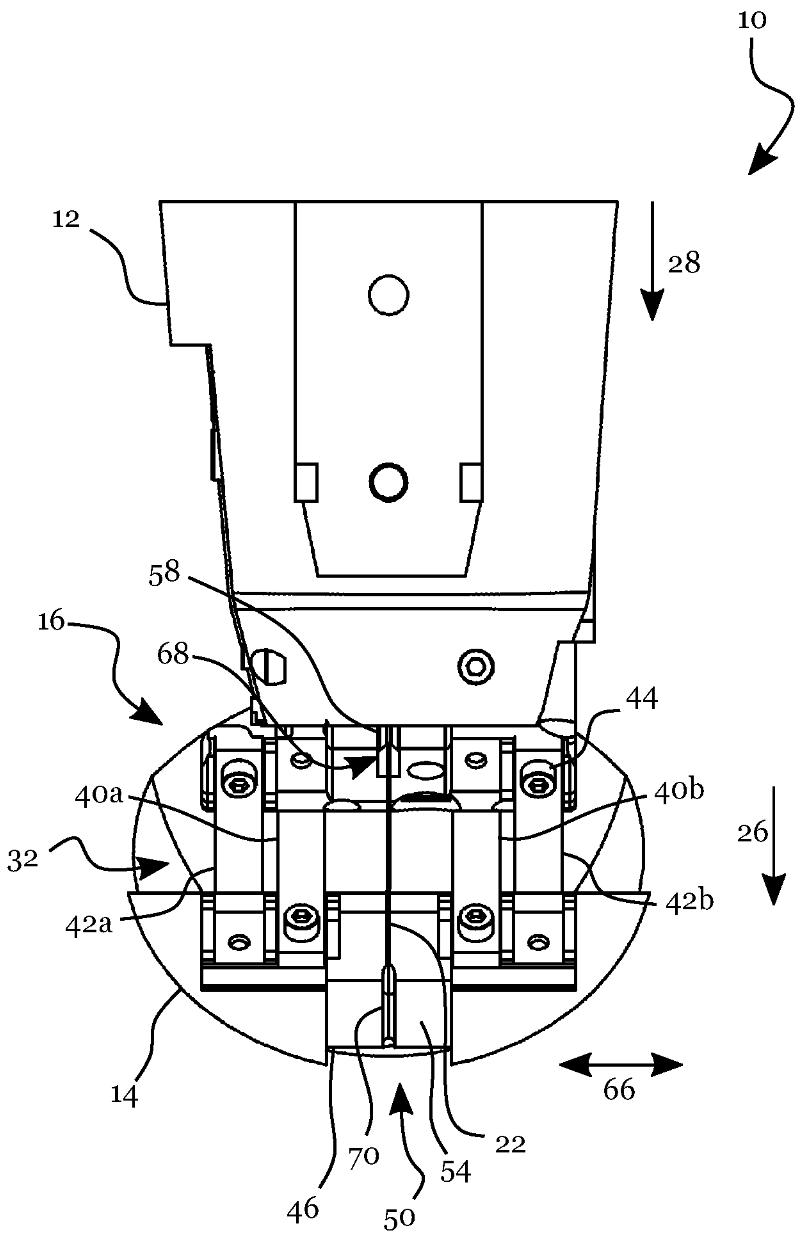
FIG. 4 illustrates a rear view of an example of an artificial joint.

FIG. 4 illustrates a rear view of an example of an artificial joint 10, which may correspond to the artificial joint 10 of FIG. 2/3. The artificial joint 10 comprises rigid links 12, 14 rotatably connected via a compliant joint 16 comprising a cross-flexural hinge 32. The cross-flexural hinge 32 comprises four elastic bars 40*a*, 40*b*, 42*a*, 42*b*, which are spaced along the width direction 66 of the artificial joint 10, which is perpendicular to the principal plane of rotation P, and each extend between the rigid links 12, 14 and are attached to the rigid links 12, 14 on opposite sides via suitable fasteners 44.

The elastic bars 40*a*, 40*b*, 42*a*, 42*b* may form a cross-flexural pivot on either side of the compliant joint 16 in the width direction 66. A first cross-flexural pivot may be formed by a first pair of crossed elastic bars 40*a*, 42*a* on one side of the compliant joint 16, and a second cross-flexural pivot may be formed by a second pair of crossed elastic bars 40*b*, 42*b* on the other side of the compliant joint 16. The crossed elastic bars 40*a*, 42*a*, 40*b*, 42*b* may cross each other when viewed along the normal direction N of the principal plane of rotation P.

The string sections 20, 22 (only string section 22 is shown in FIG. 4) may extend between the rigid links 12, 14 and may be arranged between the two pairs of crossed elastic bars 40*a*, 42*a*, 40*b*, 42*b* in the width direction 66. As shown in FIG. 4, the string sections 20, 22 may extend from a bearing 56, 58 (only bearing 58 is shown in FIG. 4) attached at the first rigid link 12 through an opening 68 in a framework of the first rigid link 12 towards the second rigid link 14.

The second rigid link 14 may comprise a mounting support 46 with curved surfaces 52, 54 (only curved surface 54 is shown in FIG. 4) featuring channels 70 for receiving the string sections 20, 22 at opposite sides of the mounting support 46 and for guiding the string sections 20, 22 towards a mounting side 50 of the mounting support 46 opposite the first rigid link 12.

The channels 70 may prevent a sideways deflection of the string sections 20, 22 along the width direction 66 by guiding the string sections 20, 22 via lateral walls on either side of the string sections 20, 22. In FIG. 4, the channel 70 is shown as a recessed portion of the mounting support 46, but the channel 70 may equally be formed of a separate material or may be formed by lateral separators, which protrude from the curved surface 52, 54 to limit a deflection of the string sections 20, 22 along the width direction 66. Thus, when the artificial joint 10 is subject to external forces, e.g. inducing a relative torsion or out-of-plane rotation of the rigid links 12, 14 with respect to the principal plane of rotation P, the channel 70 may maintain a stability of the artificial joint 10 by limiting deflection of the string sections 20, 22. In some embodiments, the first rigid link 12 may equally feature channels 70 for guiding the string sections 20, 22, e.g. in addition to or instead of the bearings 56, 58.

In some embodiments, bearings, e.g. similar to the bearings 52, 54, may be arranged at the second rigid link 14, such as to implement an elastic mounting of the string sections 20, 22 to the mounting support 46. For example, at least one bearing 52, 54 may be configured to receive a respective one of the string sections 20, 22 at the second rigid link 14, and the at least one bearing 52, 54 may be coupled to the mounting support 46 via an elastic element. Thus, the artificial joint 10 may also provide compliance with respect to a rotation in the principal plane of rotation P, e.g. despite the length of the string sections 20, 22 being effectively fixed by an actuation chain.

Figure 5:
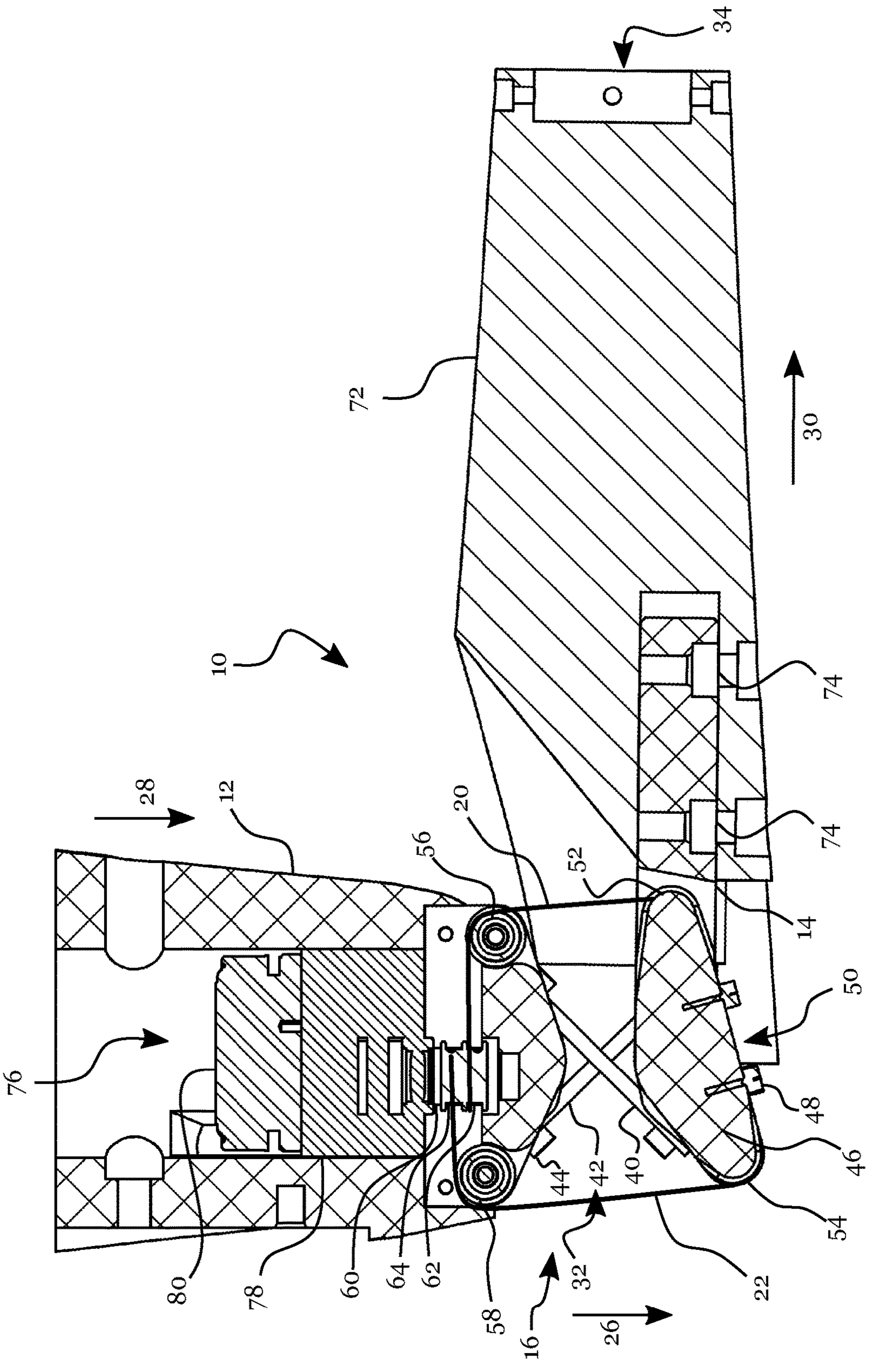
FIG. 5 illustrates a sectional sideview of an example of an artificial joint in an exemplary prosthesis.

FIG. 5 illustrates a sectional sideview of an example of an artificial joint to, illustrating the artificial joint to of FIG. 3 in a prosthesis similar to the example of FIG. 2. As shown in FIG. 5, the second rigid link 14 can be a composite link and a portion of the second rigid link 14 connected to the mounting support 46 may extend into a prosthesis part 72 of the second rigid link 14, whose profile corresponds to a human lower arm and features a mounting section 34 for attaching a wrist and/or hand prosthesis. The prosthesis part 72 may be fastened to the mounting support 46 at fastening sections 74 using suitable fasteners, such as screws (not shown).

The first rigid link 12 may equally feature a composite structure and further comprises an internal space 76 for housing a driving assembly of the artificial joint to. In the illustrated example, a gearbox 78 is arranged inside of the internal space 76 of the first rigid link 12 and is coupled to the spindle 60 and an electric motor 80 for transferring a torque of the electric motor 80 to the spindle 60 at a suitable transmission, e.g. at a ratio of greater than 10 or greater than 20. The inventors observed suitable performance for driving an elbow joint prosthesis with a brushless electric motor with a power of 30 W, with a nominal speed of about 3000 rpm, a nominal torque of about 60 mNm (max. continuous torque) and a Stall torque of about 260 mNm in conjunction with a gearbox featuring a 32:1 transmission.

The structure of the artificial joint 10 and the corresponding prosthesis may be robust and lightweight, wherein several or all of the components may be manufactured using additive fabrication methods, such as 3D printing. For example, the elastic bars 40*a*, 40*b*, 42*a*, 42*b* may be made of 3D-printed thermoplastic polyurethane, and the rigid parts 12, 14 may be made of 3D printed Polylactic acid (PLA), and may in principle be printed together as a single piece.

In addition, the proposed artificial joint design can allow a high level of customization according with the user needs. For example, the level of stiffness of the cross-flexural hinge 32 can be optimized and customized according to user requirements. The control mechanisms can range from myoelectric to a body powered harness (with and without the use of an actuator), and can be selected according to user preference and needs.

Moreover, the system can be used also as passive prosthesis with compliant behavior, wherein the string sections 20, 22 may be used to fix a current flexion state of the elbow prosthesis, or a locking pin may extend from one rigid link 12, 14 to the other to selectively lock a current flexion state of the passive prosthesis including the cross-flexural hinge 32.

It is noted that in the illustrated examples, the shortening and lengthening of the string sections 20, 22 is coupled, such that a degree of shortening/lengthening of the string sections 20, 22 is opposite and of the same magnitude. However, the string sections 20, 22 may also be shortened/lengthened at a different rate, e.g. using a suitable transmission, and may also be independently driven, such as via separate actuators for shortening/lengthening each string section 20, 22. The separate actuators may be concurrently driven, e.g. using control signals from the circuit board 38, which may be generated based on sensed myoelectric signals or based on a state of a body powered harness.

Moreover, although the cross-flexural pivots of the cross-flexural hinge 32 are shown as separate elastic elements with two individual elastic bars 40*a*, 40*b*, 42*a*, 42*b*, the elastic link 18 may also be implemented as a single piece which features elastic portions on either side of the compliant joint 16 implementing two elastic elements spaced along the width direction 66. In some embodiments, the elastic elements are joined close to the middle section 24 of the compliant joint 16.

The skilled person will further appreciate that the invention has been mainly illustrated using examples of prostheses, in particular an elbow joint prosthesis, but the features of the examples should not be understood as limited to this illustrative application, but may generally be applicable to other upper body joint prostheses, such as for replacing finger joints or wrist joints. Further, the skilled person will appreciate that the invention may also be used for implementing joints of a robotic manipulator in a robot, such as a robot for executing human tasks conventionally done with the help of the upper limb extremities or for interacting with a human.

The description of the preferred embodiments and the figures merely serve to illustrate the invention and the beneficial effects associated therewith, but should not be understood to imply any limitation. The scope of the invention is to be determined solely by the appended claims.

LIST OF REFERENCE SIGNS

10 to artificial joint
12 first rigid link
14 second rigid link
16 compliant joint
18 elastic link
20 first string section
22 second string section
24 middle section
26 spacing direction
28 main axis of first rigid link
30 main axis of the second rigid link
32 cross-flexural hinge
34 mounting section of the second rigid link
36 mounting section of the first rigid link
38 circuit board
40, 40*a, b* first elastic bar
42, 42*a, b* second elastic bar
44 fasteners
46 mounting support
48 fasteners
50 mounting side
52 first curved side
54 second curved side
56 first bearing
58 second bearing
60 spindle
62 first pulley
64 second pulley
66 width direction
68 opening
70 channel
72 prosthesis part
74 fastening section
76 internal space
78 gearbox
80 electric motor

The invention claimed is:

1. An artificial joint for a prosthesis or robot arm, the artificial joint comprising:

a first rigid link, a second rigid link, a compliant joint rotatably connecting the first rigid link and the second rigid link and defining an elastic hinge for relative rotation of the first rigid link and the second rigid link in a principal plane of rotation, and comprising an elastic link extending between the first rigid link and the second rigid link, wherein rotating the first rigid link and the second rigid link with respect to each other in the principal plane of rotation deforms the elastic link, and a first string section and a second string section both extending between the first rigid link and the second rigid link, being fixed to the second rigid link, and being arranged on opposite sides with respect to the compliant joint, such that shortening one of the first string section and of the second string section and lengthening the other one of the first string section and of the second string section drives a rotation of the first rigid link and the second rigid link with respect to each other in the principal plane of rotation.

2. The artificial joint of claim 1, wherein the compliant joint is compliant in an out-of-plane direction with respect to the principal plane of rotation to permit an out-of-plane rotation of the first rigid link and the second rigid link in response to an external force acting on the artificial joint.

3. The artificial joint of claim 1, wherein the elastic link comprises a first elastic element, and a second elastic element, wherein the first elastic element and the second elastic element each extend between the first rigid link and the second rigid link, and wherein rotating the first rigid link and the second rigid link with respect to each other in the principal plane of rotation deforms the first elastic element and the second elastic element.

4. The artificial joint of claim 3, wherein the first elastic element and the second elastic element are implemented as a cross-flexural hinge defining a hinged connection for rotation of the first rigid link and the second rigid link in the principal plane of rotation.

5. The artificial joint of claim 3, wherein the first elastic element and the second elastic element are offset from each other along the normal of the principal plane of rotation, the normal being the vector which is perpendicular to the principal plane of rotation and points out of the principal plane of rotation.

6. The artificial joint of claim 3, wherein the first string section and the second string section are arranged between the first elastic element and the second elastic element.

7. The artificial joint of claim 3, wherein each of the first elastic element and the second elastic element comprises a first elastic bar and a second elastic bar extending between the first rigid link and the second rigid link, wherein the first elastic bar and the second elastic bar cross each other, when viewed along the normal of the principal plane of rotation, the normal being the vector which is perpendicular to the principal plane of rotation and points out of the principal plane of rotation.

8. The artificial joint of claim 1, wherein the elastic link is configured to bias the first rigid link and the second rigid link towards a rest position, in which the first rigid link and the second rigid link are at a predefined rest angle to each other, wherein the predefined rest angle is between 30° and 150°.

9. The artificial joint of claim 1, further comprising an electric motor configured to drive a shortening of one or both of the first string section and of the second string section to drive the rotation of the first rigid link and the second rigid link with respect to each other in the principal plane of rotation.

10. The artificial joint of claim 1, further comprising a spindle arranged in the first rigid link and coupled to a first pulley and a second pulley connected to the first string section and the second string section, respectively, such that rotating the spindle winds up one of the first string section and of the second string section on the respective one of the first pulley and the second pulley and unwinds the other one of the first string section and of the second string section from the respective other one of the first pulley and the second pulley, for driving a rotation of the first rigid link and the second rigid link with respect to each other around the compliant joint.

11. The artificial joint of claim 1, wherein the first rigid link and the second rigid link are rotatably connected over a pre-determined range of angular motion, wherein the second rigid link comprises a first channel and second channel for guiding the first string section and the second string section, respectively, to respective mounting positions, wherein the respective mounting positions are on a side of the second rigid link, which is opposite to a side facing the first rigid link.

12. The artificial joint of claim 1, wherein the artificial joint is configured for replacing an elbow joint as part of a prosthesis, wherein the first rigid link is a proximal prosthesis part and the second rigid link is a distal prosthesis part.

13. The artificial joint of claim 1, wherein the artificial joint further comprises a first bearing and a second bearing mounted on opposite sides of the first rigid link in the principal plane of rotation, the first bearing and the second bearing being configured to receive the first string section and the second string section, respectively, extending from the second rigid link towards the first rigid link, wherein the first bearing and the second bearing are spaced along an axis of the spindle with respect to each other in accordance with a spacing of the first pulley and the second pulley along the spindle.

14. A prosthesis, the prosthesis comprising:

a first rigid link;

a second rigid link;

a joint arranged between an end of the first rigid link and an end of the second rigid link and configured to enable a rotational movement between the first rigid link and the second rigid link with respect to each other;

a first string section and a second string section extending from the first rigid link to the second rigid link, being both fixed to the second rigid link, and arranged on opposite sides of the joint, a spindle arranged in the first rigid link and coupled to a first pulley and a second pulley connected to the first string section and the second string section, respectively, the first string section and the second string section being wound on the respective pulley in opposite winding directions, such that rotating the spindle winds up one of the first string section and of the second string section on the respective one of the first pulley and the second pulley and unwinds the other one of the first string section and of the second string section from the respective other one of the first pulley and the second pulley, for driving a rotation of the first rigid link and the second rigid link with respect to each other around the joint, wherein first rigid link is configured as an upper arm prosthesis or part thereof, wherein the end of the first rigid link corresponds to a distal portion of the humerus, and the second rigid link is configured as a lower arm prosthesis or part thereof and the end of the second rigid link corresponds to a proximal portion of the ulna and radius.

15. The prosthesis of claim 14, further comprising an electric motor configured to drive a rotation of the spindle to drive the rotation of the first rigid link and the second rigid link with respect to each other in the principal plane of rotation.

16. The prosthesis of claim 14, further comprising a first bearing and a second bearing mounted on opposite sides of the first rigid link in the principal plane of rotation, the first bearing and the second bearing being configured to receive the first string section and the second string section, respectively, extending from the second rigid link towards the first rigid link, wherein the first bearing and the second bearing are spaced along an axis of the spindle with respect to each other in accordance with a spacing of the first pulley and the second pulley along the spindle.

17. The prosthesis of claim 14, wherein the first string section is a ventral string section and the second string section is a dorsal string section.

18. The prosthesis of claim 14, wherein the second rigid link comprises a ventral channel and dorsal second channel for guiding the first string section and the second string section to respective mounting positions, wherein the respective mounting positions are on a side of the second rigid link, which is opposite to a side facing the first rigid link.

19. A passive joint prosthesis comprising a first rigid link, a second rigid link, a pair of cross-flexural pivots extending between the first rigid link and the second rigid link for defining a cross flexural hinge with a principal plane of rotation, the cross-flexural pivots being spaced along the normal of the principal plane of rotation from each other, the normal being the vector which is perpendicular to the principal plane of rotation and points out of the principal plane of rotation;

wherein each of the cross flexural pivots comprises a first elastic bar and a second elastic bar extending between the first rigid link and the second rigid link, wherein the first elastic bar and the second elastic bar cross each other, when viewed along the normal of the principal plane of rotation; and a locking mechanism for selectively restraining a rotation of the first rigid link with respect to the second rigid link in the principal plane of rotation.

* * * * *